(12) United States Patent
Jung et al.

(10) Patent No.: US 12,109,123 B2
(45) Date of Patent: Oct. 8, 2024

(54) INTERVERTEBRAL FUSION CAGE

(71) Applicants: CG BIO CO., LTD., Seongnam-si (KR); SEOUL NATIONAL UNIVERSITY HOSPITAL, Seoul (KR)

(72) Inventors: Ui Su Jung, Seoul (KR); Seung Jae Hyun, Seoul (KR)

(73) Assignees: CG BIO CO., LTD., Seongnam-si (KR); SEOUL NATIONAL UNIVERSITY HOSPITAL, Seoul (KR)

( * ) Notice: Subject to any disclaimer, the term of this patent is extended or adjusted under 35 U.S.C. 154(b) by 273 days.

(21) Appl. No.: 17/765,126

(22) PCT Filed: Sep. 29, 2020

(86) PCT No.: PCT/KR2020/013343
§ 371 (c)(1),
(2) Date: Mar. 30, 2022

(87) PCT Pub. No.: WO2021/066524
PCT Pub. Date: Apr. 8, 2021

(65) Prior Publication Data
US 2022/0395383 A1  Dec. 15, 2022

(30) Foreign Application Priority Data
Sep. 30, 2019 (KR) .......... 10-2019-0120578

(51) Int. Cl.
*A61F 2/44* (2006.01)
*A61F 2/46* (2006.01)
*A61F 2/30* (2006.01)

(52) U.S. Cl.
CPC .......... *A61F 2/4455* (2013.01); *A61F 2/4611* (2013.01); *A61F 2002/30433* (2013.01);
(Continued)

(58) Field of Classification Search
CPC ...... A61F 2/442; A61F 2/4425; A61F 2/4455; A61F 2002/443
(Continued)

(56) References Cited

U.S. PATENT DOCUMENTS 10,137,006 B2  11/2018  Dewey et al.
10,154,912 B2 * 12/2018  Glerum .................. A61F 2/442
(Continued)

FOREIGN PATENT DOCUMENTS

EP  3485850 A1  5/2019
JP  6363087 A  7/2018
(Continued)

OTHER PUBLICATIONS

Notice of Reasons for Refusal issued in JP Application No. 2022-520058 dated Mar. 14, 2023, 7 pgs.
(Continued)

*Primary Examiner* — Eduardo C Robert
*Assistant Examiner* — Christina Negrellirodriguez
(74) *Attorney, Agent, or Firm* — Rothwell, Figg, Ernst and Manbeck, P.C.

(57) ABSTRACT

An intervertebral fusion cage is disclosed. An intervertebral fusion cage according to an embodiment of the present invention comprises: a body including a receiving part of which upper and lower portions are open, an upper guide part, and a lower guide part; a moving member disposed in the receiving part; a screw which is screw-coupled to the body and moves forwards or backwards relative to the body integrally with the moving member when rotating; an upper plate which has a guided part guided by the upper guide part and is disposed above the body while being engaged with the moving member; and a lower plate which has a guided part guided by the lower guide part and is disposed under the body while being engaged with the moving member.

12 Claims, 10 Drawing Sheets

(52) U.S. Cl.
CPC ............... *A61F 2002/30556* (2013.01); *A61F 2002/30579* (2013.01); *A61F 2002/4627* (2013.01)

(58) Field of Classification Search
USPC .......................................... 623/17.11–17.16
See application file for complete search history.

(56) References Cited

U.S. PATENT DOCUMENTS

| | | | |
|---|---|---|---|
| 11,382,761 B2* | 7/2022 | Altarac | ................... A61F 2/442 |
| 2007/0270968 A1* | 11/2007 | Baynham | ................ A61F 2/447 |
| | | | 623/17.11 |
| 2015/0173917 A1 | 6/2015 | Radcliffe et al. | |
| 2015/0342748 A1 | 12/2015 | Baynham | |
| 2019/0021868 A1* | 1/2019 | Ludwig | ................ A61F 2/4611 |

FOREIGN PATENT DOCUMENTS

| | | | |
|---|---|---|---|
| JP | 2019503238 A | 2/2019 |
| JP | 2019088791 A | 6/2019 |
| KR | 10-1371418 B1 | 3/2014 |

OTHER PUBLICATIONS

International Search Report Issued in PCT/KR2020/013343 dated Apr. 2, 2021, 11 pages.

* cited by examiner

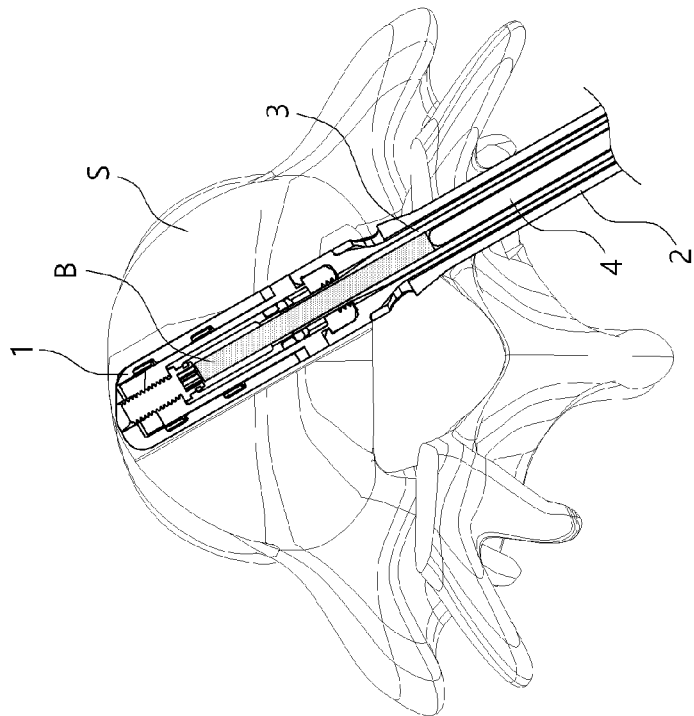
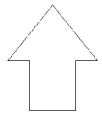
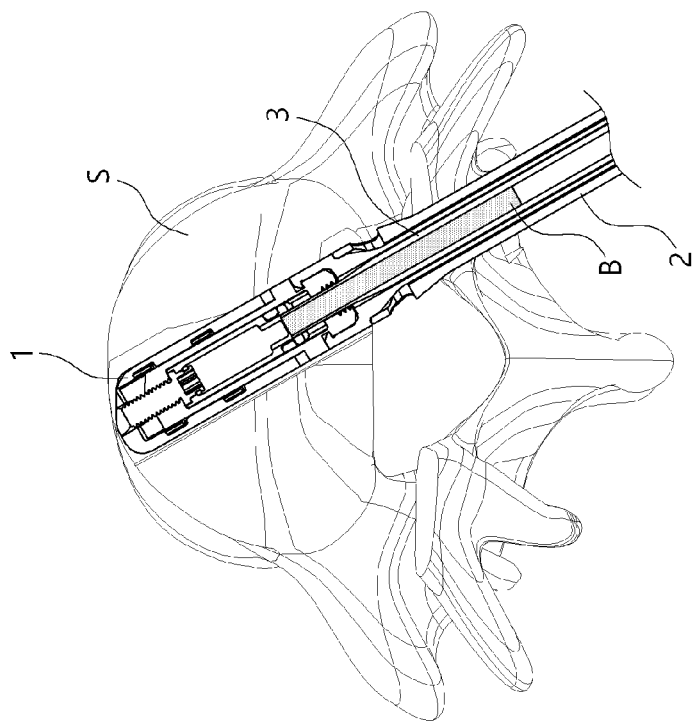
FIG. 11

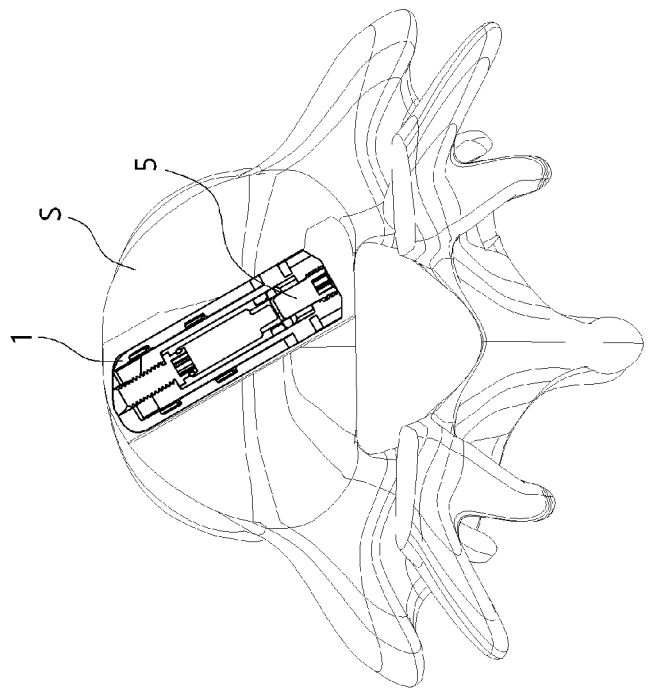
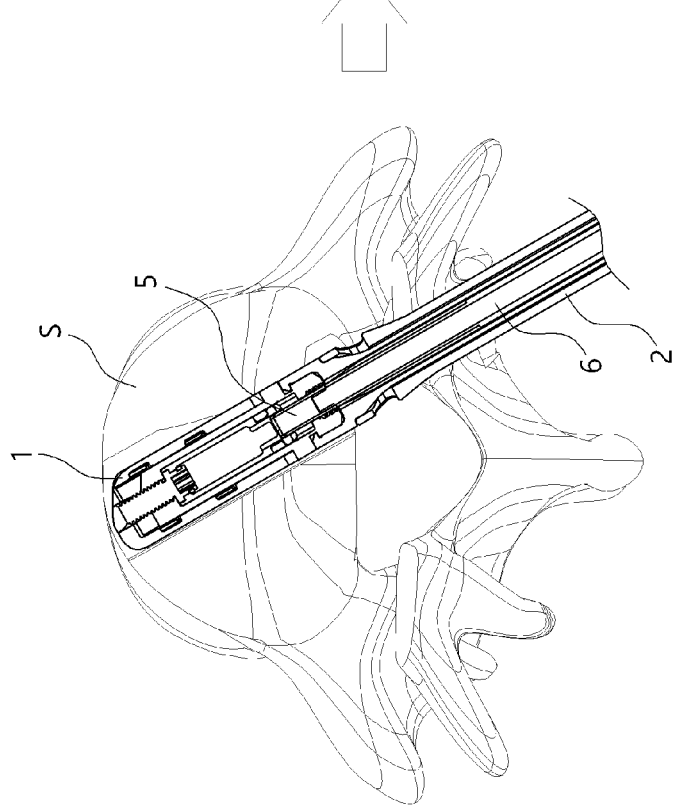
FIG. 13

INTERVERTEBRAL FUSION CAGE

CROSS-REFERENCE TO RELATED APPLICATION

This application is a 35 U.S.C. 371 National Phase Entry Application from PCT/KR2020/013343, filed Sep. 29, 2020, which claims priority to and the benefit of Korean Patent Application No. 10-2019-0120578, filed on Sep. 30, 2019, the disclosures of which are incorporated herein by reference in their entireties.

TECHNICAL FIELD

The present invention relates to an intervertebral fusion cage, and more particularly, to an intervertebral fusion cage that is inserted into a space from which a disc is removed to secure a gap between adjacent vertebral bodies.

BACKGROUND

The intervertebral fusion cage is a device used for fusion, which is a surgical treatment method for spinal diseases. When a disc is ruptured or weakened due to a disease or accident, it compresses the spinal nerve and causes pain, and in this case, the damaged disc is removed, and the intervertebral fusion is performed by inserting an intervertebral fusion cage that restores and maintains the gap and lordosis between the vertebrae in the intervertebral body from which the damaged area has been removed.

As described above, the intervertebral fusion cage is inserted into the intervertebral body between the vertebrae from which the degenerative disc has been removed to secure a space for the bone to grow for fusion. In addition, the intervertebral fusion cage relieves pain by securing a gap between the vertebral bodies, and restores the stability of the spine.

Conventionally, PEEK/Titanium intervertebral fusion cage has been widely used. In general, in the case of PEEK/Titanium intervertebral fusion cage, each product has a fixed size and height. Therefore, it is virtually impossible to properly secure the gap between vertebrae that differs depending on the patient by patient customization. In addition, it was not easy to insert the intervertebral fusion cage when the disc space between the vertebrae of the patient was narrow.

In order to solve this problem, an intervertebral fusion cage that can be adjusted in height is being introduced, but the existing products have a structure in which the components for height adjustment upon height expansion gather in the center of the interior or move in one direction to contract, and so there is a problem in that it is difficult to secure a space to fill a bone graft material because the internal space is cramped. In addition, if the intervertebral fusion cage filled with a bone graft material is implanted in a patient's body and thereafter the height thereof is expanded, it is also pointed out as a problem that it is impossible to additionally fill the expanded space with a bone graft material.

Meanwhile, in general, the intervertebral fusion cage is inserted obliquely with respect to the coronal plane of a human body when inserted into the intervertebral body. However, since the conventional intervertebral fusion cage has a square structure symmetrical left and right, it is difficult to push it to the frontmost part of the curved intervertebral body. Accordingly, the keels formed on the upper and lower portions of the intervertebral fusion cage may not be arranged horizontally with respect to the coronal plane, which may cause instability during the fusion of the intervertebral body.

(Related Art Document) Korean Patent Registration No. 10-1371418 "INTERVERTEBRAL FUSION DEVICE"

SUMMARY

Technical Problem

The present invention is to solve the problems of the related art described above.

One aspect of the present invention is directed to providing an intervertebral fusion cage that is inserted into the intervertebral body to secure a gap between vertebral bodies, wherein the height of the intervertebral fusion cage can be adjusted on a continuous scale, enabling a patient-specific fusion and reducing the burden on the surgeon during the surgical procedure.

Another aspect of the present invention is directed to providing an intervertebral fusion cage having a structure suitable for pushing it to the frontmost part of the intervertebral body, thereby ensuring physical stability during intervertebral body fusion.

Yet another aspect of the present invention is directed to providing an intervertebral fusion cage, which can efficiently secure a space for filling a bone graft material therein while the height can be adjusted.

The aspect of the present invention is not limited thereto, and other aspects not mentioned will be clearly understood by those of ordinary skill in the art from the following description.

Technical Solution

According to an aspect of the present invention, provided is an intervertebral fusion cage comprising: a body including a receiving part of which upper and lower portions are open, an upper guide part, and a lower guide part; a moving member disposed in the receiving part; a screw which is screw-coupled to the body and moves forwards or backwards relative to the body integrally with the moving member when rotating; an upper plate which has a guided part guided by the upper guide part and is disposed above the body while being engaged with the moving member; and a lower plate which has a guided part guided by the lower guide part and is disposed under the body while being engaged with the moving member.

In this case, when the screw is rotated in one direction while the upper plate and the lower plate are fixed between the human body's vertebral bodies, as the body moves forward by the screw and the moving member, the upper plate may move upward along the upper guide part and the lower plate may move downward along the lower guide part.

In addition, the upper guide part may be formed in a downwardly inclined form from the rear to the front in the upper portion of the body, and the lower guide part may be formed in an upwardly inclined form from the rear to the front in the lower portion of the body.

In addition, the body may further include a screw hole formed in the front of the body, and the screw may include a head part rotatably coupled to the moving member and a screw thread part screwed to the screw hole.

In addition, the moving member may be formed in a shape that is surrounded on all sides by sidewalls and is open up and down, and may include a screw coupling hole formed so that the head part penetrates and is coupled to the front sidewall.

In addition, the body may further include a rear hole formed through the rear in communication with the receiving part, and the moving member may further include a guide hole formed through the rear sidewall so that a screw rotation tool passing through the rear hole can enter the head part.

In addition, the rear hole may provide a coupling interface of a surgical tool for insertion of the intervertebral fusion cage into the human body.

In addition, the moving member may include grooves formed in the vertical direction on opposite sidewalls, respectively, and the upper plate and the lower plate may include a protrusion inserted into the groove, respectively.

In addition, the upper guide part and the lower guide part may be formed on opposite sides of the body, respectively.

In addition, the upper plate and the lower plate may include front inclined parts formed to protrude forward from one side to the other side at the front.

In addition, the upper plate and the lower plate are formed vertically symmetrical.

In addition, the upper plate and the lower plate may include a keel part formed parallel to the front inclined part at the upper portion and the lower portion, respectively.

In addition, the upper plate and the lower plate may include window parts, respectively, penetrated in the vertical direction.

In addition, the body may be formed to be surrounded on all sides by sidewalls and open up and down.

Advantageous Effects

According to an embodiment of the present invention, the height of the intervertebral fusion cage inserted into the intervertebral body can be adjusted on a continuous scale, enabling a patient-specific fusion and reducing the burden on the surgeon during the surgical procedure.

In addition, physical stability can be secured during intervertebral body fusion through the intervertebral fusion cage having a structure suitable for pushing it to the frontmost part of the intervertebral body.

In addition, even after adjusting the height of the intervertebral fusion cage, it is possible to efficiently secure a space for filling the bone graft material therein.

BRIEF DESCRIPTION OF THE DRAWINGS

The above and other aspects, features, and advantages of the present invention will become more apparent to those of ordinary skill in the art by describing embodiments thereof in detail with reference to the accompanying drawings, in which:

FIG. 11 is a view showing a process of inserting an intervertebral fusion cage according to an exemplary embodiment of the present invention into a human body and injecting a bone graft material.

FIG. 13 is a view showing a process of coupling a locking screw after inserting an intervertebral fusion cage according to an exemplary embodiment of the present invention into a human body and injecting a bone graft material.

DETAILED DESCRIPTION OF THE EMBODIMENTS

Figure 1:
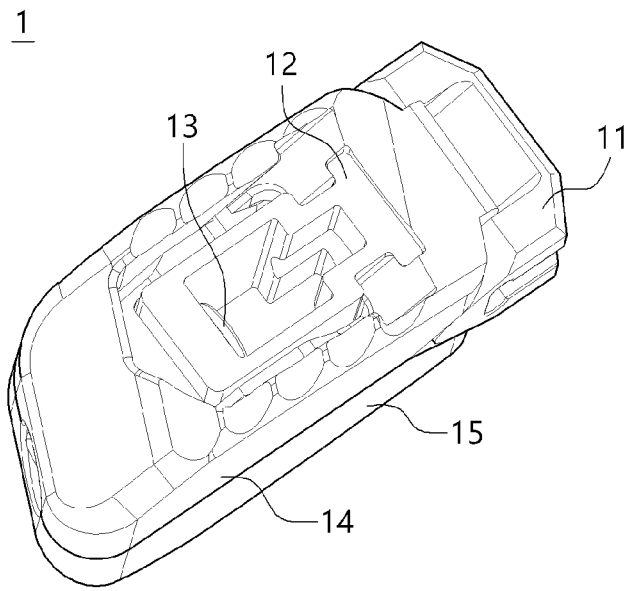
FIG. 1 is a perspective view of an intervertebral fusion cage according to an exemplary embodiment of the present invention.

Hereinafter, exemplary embodiments of the present invention will be described in detail so that those of ordinary skill in the art can readily implement the present invention with reference to the accompanying drawings. The present invention may be embodied in many different forms and is not limited to the embodiments set forth herein. In the drawings, parts unrelated to the description are omitted for clarity of description of the present invention, and throughout the specification, like reference numerals denote like elements.

It is understood that the terms "comprise" or "have" when used in this specification, are intended to specify the presence of stated features, integers, steps, operations, elements, components and/or a combination thereof but not preclude the possibility of the presence or addition of one or more other features, integers, steps, operations, elements, components, or a combination thereof.

Figure 2:
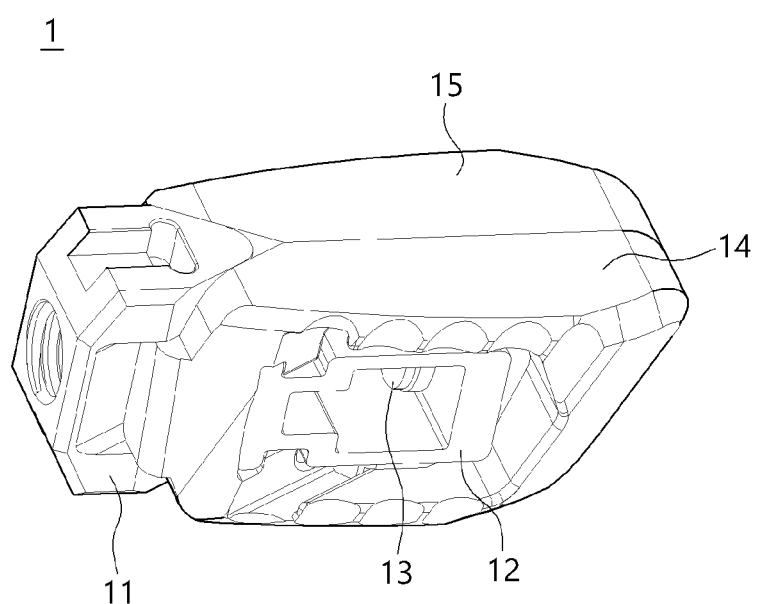
FIG. 2 is a perspective view showing an intervertebral fusion cage according to an exemplary embodiment of the present invention from another angle.
Figure 3:
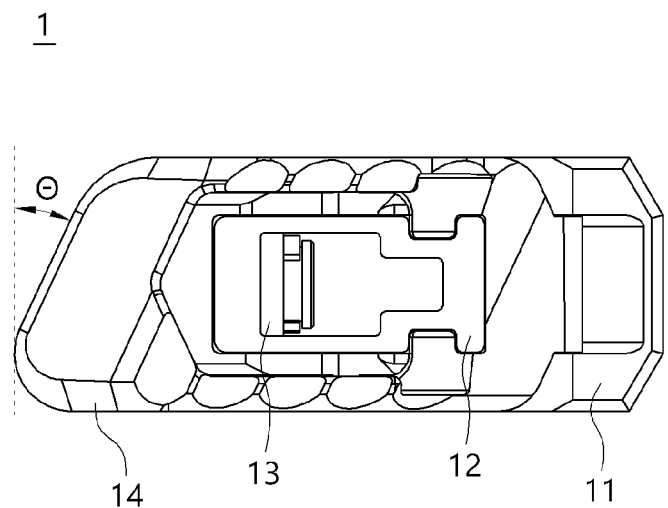
FIG. 3 is a top plan view of an intervertebral fusion cage according to an exemplary embodiment of the present invention.
Figure 4:
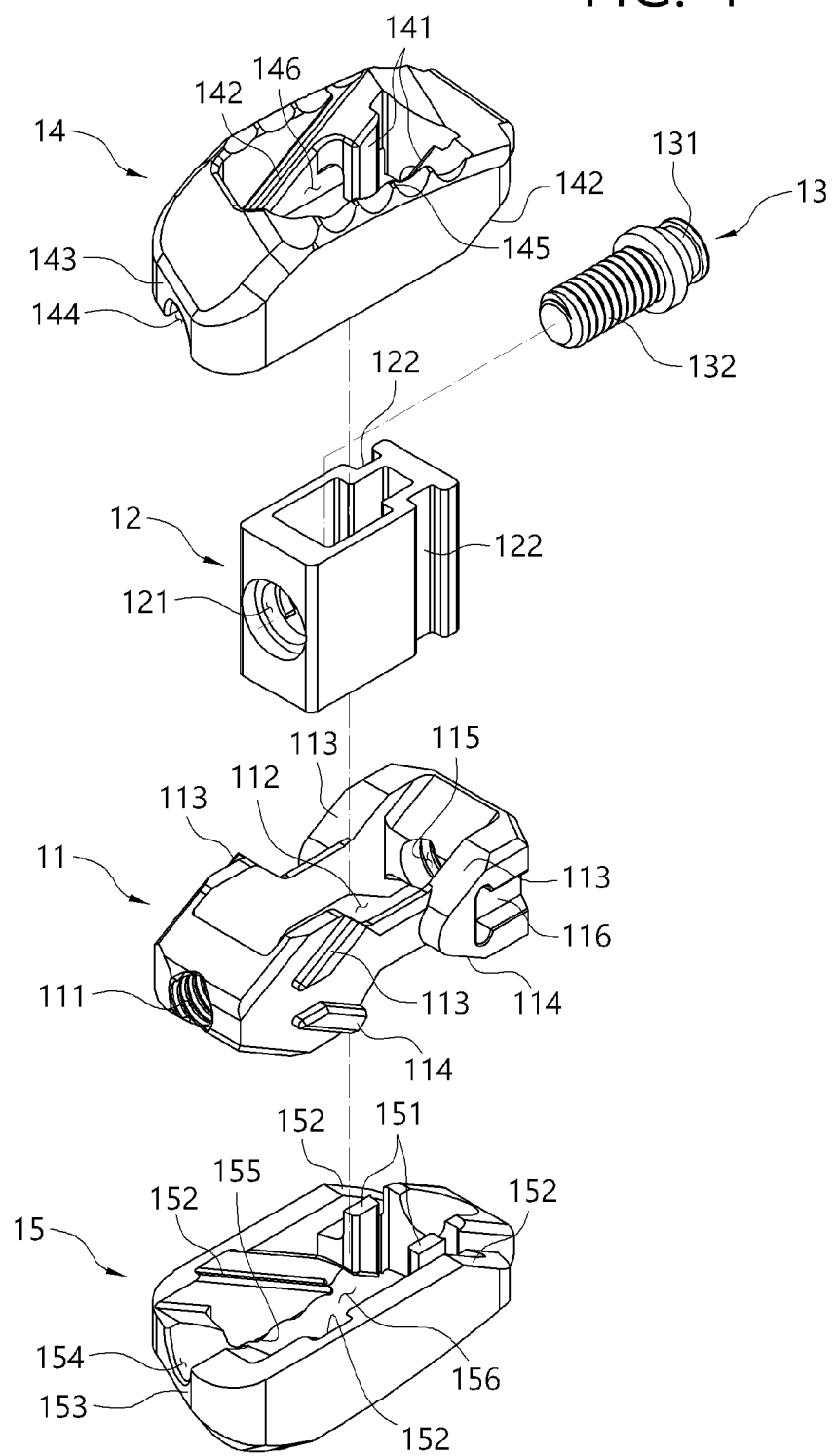
FIG. 4 is an exploded perspective view of an intervertebral fusion cage according to an exemplary embodiment of the present invention.
Figure 5:
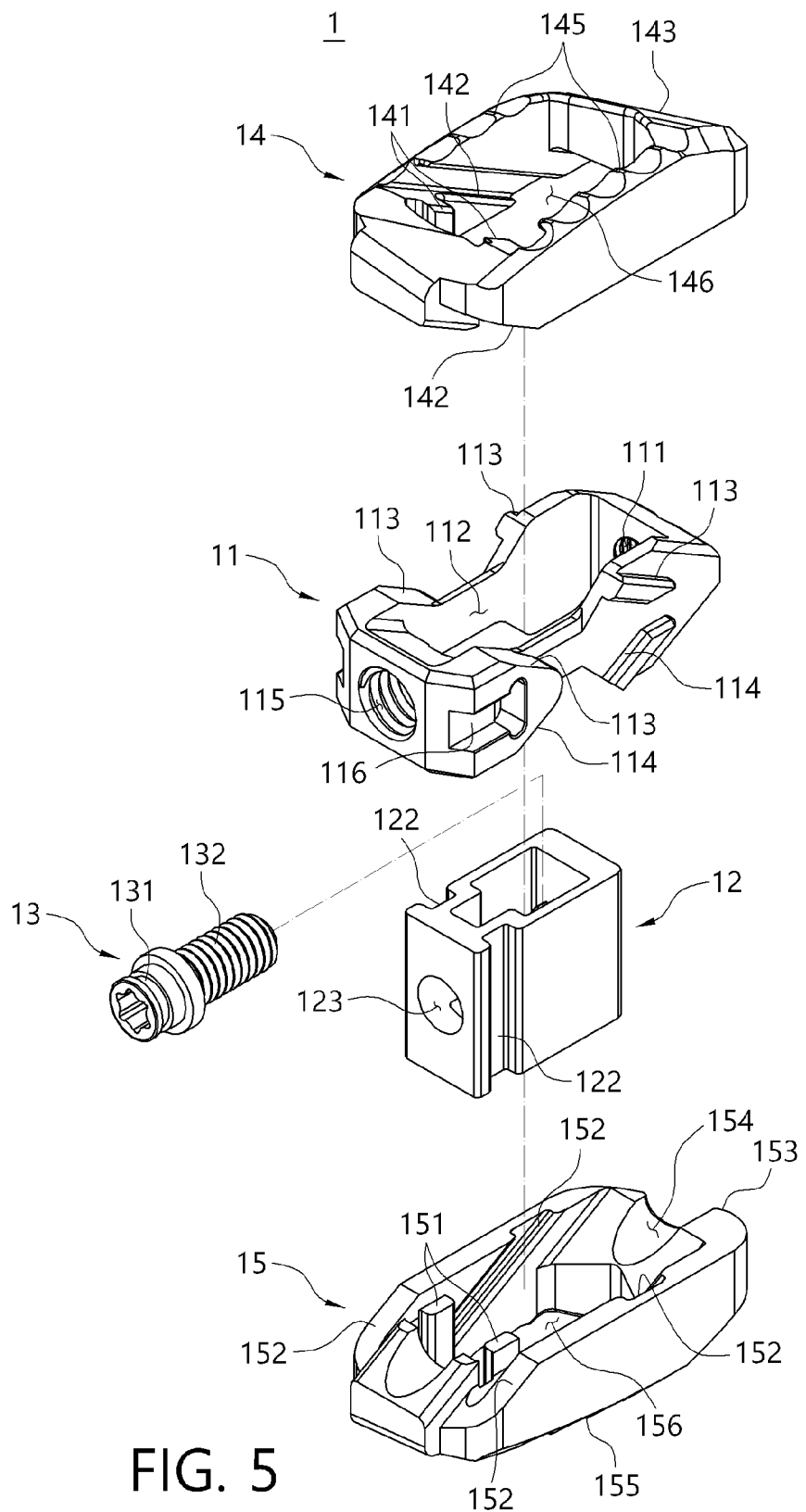
FIG. 5 is an exploded perspective view showing an intervertebral fusion cage according to an exemplary embodiment of the present invention from another angle.

FIGS. 1 and 2 shows a perspective view seen from above and a perspective view seen from below, respectively, of an intervertebral fusion cage according to an exemplary embodiment of the present invention, and FIG. 3 shows a top plan view of an intervertebral fusion cage according to an exemplary embodiment of the present invention. In addition, FIGS. 4 and 5 shows an exploded perspective view seen from the front and an exploded perspective view seen from the rear, respectively, of an intervertebral fusion cage according to an exemplary embodiment of the present invention.

Referring to FIGS. 1 to 5, an intervertebral fusion cage 1 according to an exemplary embodiment of the present invention includes a body 11, a moving member 12, a screw 13, an upper plate 14, and a lower plate 15.

The body 11 is a portion in which the moving member 12, the screw 13, the upper plate 14, and the lower plate 15 are disposed. The body 11 has a frame shape that is surrounded on all sides by sidewalls and is open up and down.

In an embodiment of the present invention, the body 11 includes a screw hole 111, a receiving part 112, an upper guide part 113, a lower guide part 114, a rear hole 115, and an inserter coupling part 116.

The screw hole 111 is formed in the front of the body 11. The screw hole 11 is a portion to which a screw thread part 132 of the screw 13 is coupled, and is formed complementary to the screw thread part 132 of the screw 13. In an embodiment of the present invention, the screw hole 111 is formed through the front side all of the body 11.

The receiving part 112 is formed in communication with the screw hole 111 at the rear of the screw hole 111. The receiving part 112 is formed in the center of the body 11 as an open space up and down. The moving member 12, the screw 13, etc. are disposed in the receiving part 112, and after the intervertebral fusion cage according to an exemplary embodiment of the present invention is into the space from which the disc is removed in a patient's spine, the bone graft material may be filled through the empty space of the receiving unit 112.

The upper guide part 113 and the lower guide part 114 are in contact with the guided part 142 of the upper plate 14 and the guided part 152 of the lower plate 15, respectively. As will be described in detail later, when the screw 13 rotates in one direction and the moving member 12 moves backward relative to the body 11, the upper plate 14 is pushed up by the upper guide part 113, and the lower plate 15 is pushed down by the lower guide part 114.

In an embodiment of the present invention, the upper guide part 113 is formed in a downwardly inclined form from the rear to the front in the upper portion of the body 11, and the lower guide part 114 is formed in an upwardly inclined form from the rear to the front in the lower portion of the body 11. That is, in an embodiment of the present invention, the upper guide part 113 and the lower guide part 114 are formed as inclined parts symmetrical to each other.

The upper guide part 113 and the lower guide part 114 may be formed in plurality for smooth vertical movement of the upper plate 14 and the lower plate 15, or may be formed on opposite sides of the body 11. It is preferable in terms of left-right balance that the upper guide part 113 and the lower guide part 114 are formed symmetrically. As shown in detail in FIGS. 4 and 5, in an embodiment of the present invention, the upper guide part 113 and the lower guide part 114 are symmetrically formed on the left and right sidewalls of the body 11, and are formed in pairs on the front and rear sides, respectively.

The rear hole 115 communicates with the receiving part 112 and is formed through the rear. In an embodiment of the present invention, the rear hole 115 is formed through the rear sidewall of the body 11. After the intervertebral fusion cage 1 according to an exemplary embodiment of the present invention is inserted into a surgical site, a screw rotation tool for rotation of the screw 13 may enter the receiving part 112 through the rear hole 115.

In addition, the rear hole 115 may function as an interface to which a surgical instrument for insertion of the intervertebral fusion cage 1 according to an exemplary embodiment of the present invention into the human body is coupled. In an embodiment of the present invention, the rear hole 115 is threaded on its inner circumferential surface, and in a state where the end of the surgical instrument is screwed to the rear hole 115, the intervertebral fusion cage 1 according to an exemplary embodiment of the present invention may be inserted into an intervertebral space of a patient.

The inserter coupling part 116 is a part to which the inserter 2 for insertion of the intervertebral fusion cage 1 according to an exemplary embodiment of the present invention into the human body is coupled. In an embodiment of the present invention, the inserter coupling part 116 is formed in a recess shape having a predetermined shape on opposite sidewalk of the body 11. The intervertebral fusion cage 1 may be coupled to the front of the inserter 2 by inserting the end of the inserter 2 having a protruding shape corresponding to the recess shape of the inserter coupling part 116.

The moving member 12 is disposed in the receiving part 112 and relatively moves backward or forward with respect to the body 11 together with the screw 13 when the screw 13 is rotated. As the moving member 12 moves backward or forward relative to the body 11, the upper plate 14 and the lower plate 15 engaged with the moving member 12 move up and down.

In an embodiment of the present invention, the moving member 12 is formed in a shape that is surrounded on all sides by sidewalls and is open up and down. The moving member 12 is coupled to the screw 13 and moves backward or forward together according to the backward or forward movement of the screw 13.

In an embodiment of the present invention, the moving member 12 includes a screw coupling hole 121, a groove 122, and a guide hole 123.

The screw coupling hole 121 is formed so that a head part 131 of the screw 13 is inserted and coupled to the front sidewall of the moving member 12. The screw coupling hole 121 has a shape in which the head part 131 of the screw 13 can be rotatably coupled. The moving member 12 and the screw 13 are coupled through the screw coupling hole 121, and when the screw 13 is rotated, the screw 13 and the moving member 12 also move integrally.

The grooves 122 are formed in the vertical direction on the sidewalls of opposite sides of the moving member 12. By inserting protrusions 141 of the upper plate 14 and protrusions 151 of the lower plate 15 into the grooves 122, the moving member 12 is engaged with the upper plate 14 and the lower plate 15.

The guide hole 123 is formed through the rear sidewall of the moving member 12. The guide hole 123 provides a path through which the screw rotation tool passing through the rear hole 115 of the body 11 can enter the head part 131.

Meanwhile, in an embodiment of the present invention, the central portion of the moving member 12 is formed as an empty space with open up and down, and after the intervertebral fusion cage according to an exemplary embodiment of the present invention is inserted into an intervertebral space of a patient from which the disc is removed, the bone graft material may be filled in the corresponding space.

The screw 13 is screwed to the body 11 and moves relative to the body 11 in a forward or backward direction integrally with the moving member 12 during rotation. When the screw 13 is rotated in one direction, the screw 13 and the moving member 12 move backward relative to the body 11, and when the screw 13 is rotated in the other direction, the screw 13 and the moving member 12 move forward relative to the body 11.

In an embodiment of the present invention, the screw 13 includes a head part 131 rotatably coupled to the moving member and a screw thread part 132 screwed to the screw hole 111.

The head part 131 is rotatably coupled to the screw coupling hole 121 of the moving member 12. The head part 131 is inserted and coupled to the screw coupling hole 121, and may be rotated by a screw rotation tool that enters through the guide hole 123 of the moving member 12. The head part 131 is coupled to the screw coupling hole 121 whereby the screw 13 can move integrally with the moving member 12.

The screw thread part 132 is screwed into the screw hole 111 of the body 11. In an embodiment of the present invention, the screw thread part 132 has a length capable of moving backward or forward in a predetermined range while being coupled to the screw hole 111. According to the rotation of the head part 131, the screw thread part 132 moves in a straight line while being engaged with the screw hole 111.

The upper plate 14 and the lower plate 15 are respectively disposed on the upper and lower portions of the body 11. When the screw 13 is rotated in one direction while the upper plate 14 and the lower plate 15 are fixed between a patient's vertebral bodies, as the body 11 moves forward by the screw 13 and the moving member 12, the upper plate 14 moves upward along the upper guide part 113 and the lower plate 15 moves downward along the lower guide part 114. Through this, the height of the intervertebral fusion cage 1 in the intervertebral body can be varied by patient customization.

The upper plate 14 and the lower plate 15 have protrusions 141 and 151, respectively, that are inserted into the grooves 122 of the moving member 12 to make the upper plate 14 and the lower plate 15 to engage with the moving member 12. The protrusions 141 and 151 are respectively formed on the inner surfaces of the upper plate 14 and the lower plate 15. The upper plate 14 and the lower plate 15 are engaged with the moving member 12 through the protrusions 141 and 151.

In addition, the upper plate 14 has the guided part 142 guided by the upper guide part 113, and the lower plate 15 has the guided part 152 guided by the lower guide part 114. In an embodiment of the present invention, the guided part 142 of the upper plate 14 is formed as an inclined part complementary to the upper guide part 113, and the guided part 152 of the lower plate 15 is formed as an inclined part complementary to the lower guide part 114. In addition, the guided parts 142 and 152 are formed on the inner surfaces of the upper plate 14 and the lower plate 15.

In other words, the upper plate 14 has the guided part 142 complementary to the upper guide part 113 and is engaged with the moving member 12 and disposed on the upper portion of the body 11, and the lower plate 15 has the guided part 152 complementary to the lower guide part 114 and is engaged with the moving member 12 and disposed on the lower portion of the body 11.

Figure 6:
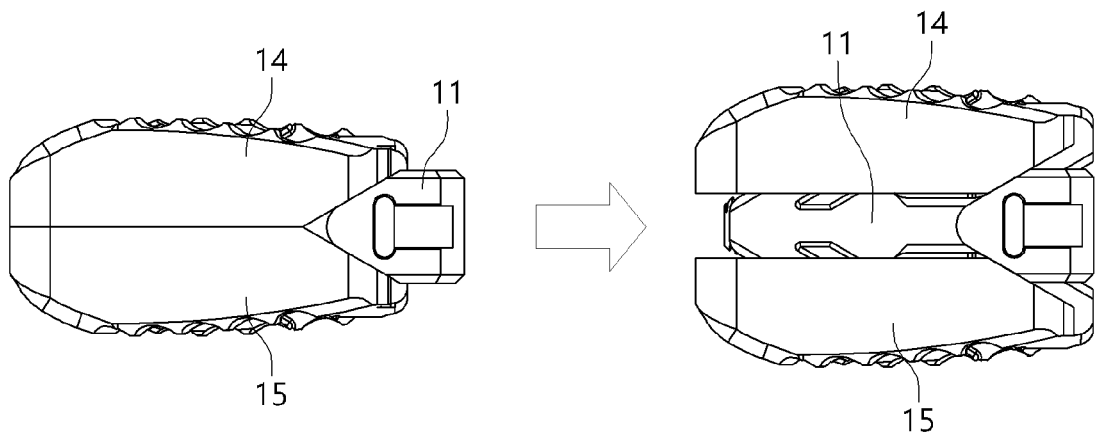
FIG. 6 is a side view showing a height adjustment process of an intervertebral fusion cage according to an exemplary embodiment of the present invention.
Figure 7:
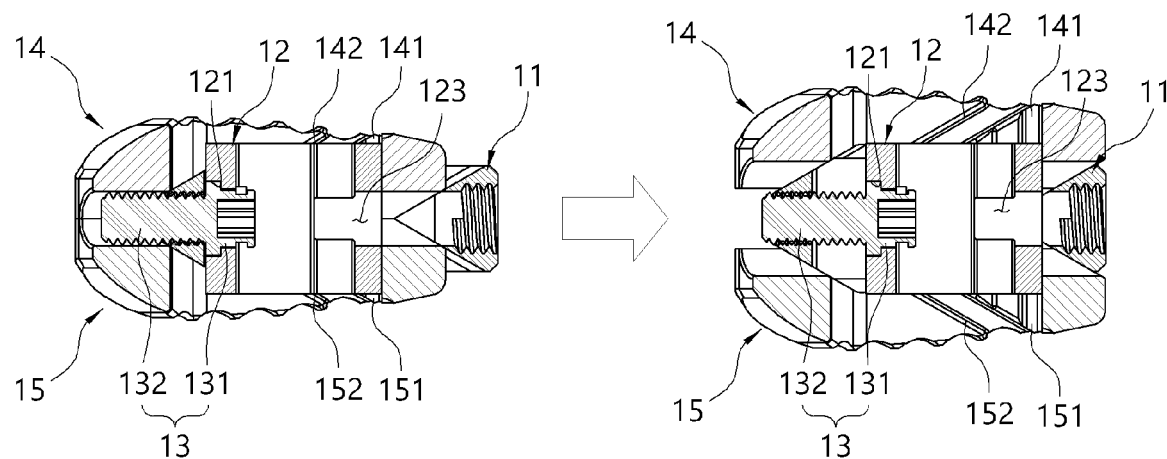
FIG. 7 is a longitudinal cross-sectional view showing a height adjustment process of an intervertebral fusion cage according to an exemplary embodiment of the present invention.
Figure 8:
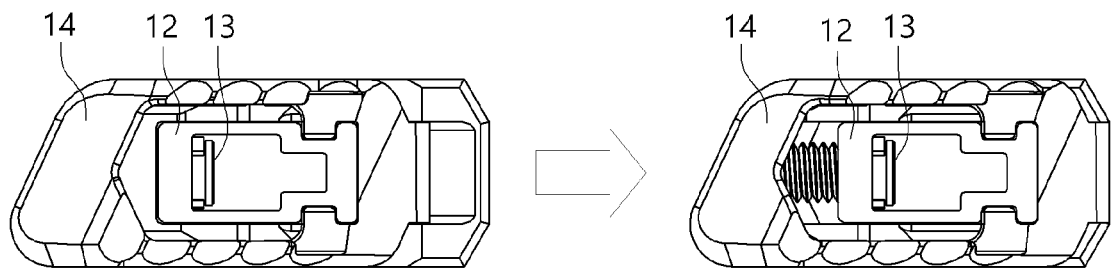
FIG. 8 is a top plan view showing a height adjustment process of an intervertebral fusion cage according to an exemplary embodiment of the present invention.

FIG. 6 is a side view showing a height adjustment process of an intervertebral fusion cage according to an exemplary embodiment of the present invention, and FIG. 7 is a longitudinal cross-sectional view showing a height adjustment process of an intervertebral fusion cage according to an exemplary embodiment of the present invention. In addition, FIG. 8 is a top plan view showing a height adjustment process of an intervertebral fusion cage according to an exemplary embodiment of the present invention.

The height adjustment process of the intervertebral fusion cage 1 according to an exemplary embodiment of the present invention will be described with reference to FIGS. 6 to 8. It is premised that the height adjustment process of the intervertebral fusion cage 1 to be described below is performed in a state in which the intervertebral fusion cage 1 is inserted into an intervertebral space from which the disc of a patients spine is removed and the upper plate 14 and the lower plate 15 are fixed by the vertebral body.

In a state in which the intervertebral fusion cage 1 is inserted into an intervertebral space from which the disc of a patient's spine is removed and the upper plate 14 and the lower plate 15 are fixed by the vertebral body, when the screw 13 is rotated in one direction, a force to move backward is applied to the screw 13 and the moving member 12. However, since the moving member 12 is engaged with the upper plate 14 and the lower plate 15, the body 11 moves forward by reaction. To describe this from another point of view, the screw 13 and the moving member 12 are relatively moved rearward with respect to the body 11 according to the one-way rotation of the screw 13.

Accordingly, the upper plate 14 engaged with the moving member 12 moves upward riding on the upper guide part 113, and the lower plate 15 moves downward riding on the lower guide part 114. As a result, the upper plate 14 moves upward and the lower plate 15 moves downward, so that the height of the intervertebral fusion cage 1 is expanded.

As such, according to an embodiment of the present invention, the vertical gap of the intervertebral fusion cage 1 can be adjusted on a continuous scale. Through this, it is easy to insert the intervertebral fusion cage 1 and secure a bone fusion space for the fusion of the vertebral body, and a patient-specific fusion can be performed suitable for the gap between the vertebral bodies of the patient.

In addition, according to an embodiment of the present invention, a space for filling the bone graft material inside is efficiently secured after height expansion. In this case, the bone graft material may be injected through the rear hole 115 at the rear of the body 11 and the guide hole 123 of the moving member 12.

Meanwhile, the upper plate 14 and the lower plate 15 include front inclined parts 143 and 153, respectively, formed to protrude forward from one side to the other side at the front. In addition, the upper plate 14 and the lower plate 15 are vertically symmetrical. As the upper plate 14 and the lower plate 15 are configured as described above, the intervertebral fusion cage 1 according to an exemplary embodiment of the present invention has a structure suitable for pushing it to the frontmost part of the intervertebral body when inserted into an intervertebral body.

Referring to FIG. 3, the front inclined parts 143 and 153 form a predetermined angle θ with the front horizontal plane. Specifically, when considering the insertion angle of the intervertebral fusion cage 1 upon TLIF (Transforaminal Lumbar Interbody Fusion) surgery, the front inclined parts 143 and 153 may form an angle of about 20 to 50° with the horizontal plane in front, and preferably an angle of 25 to 35°.

Figure 9:
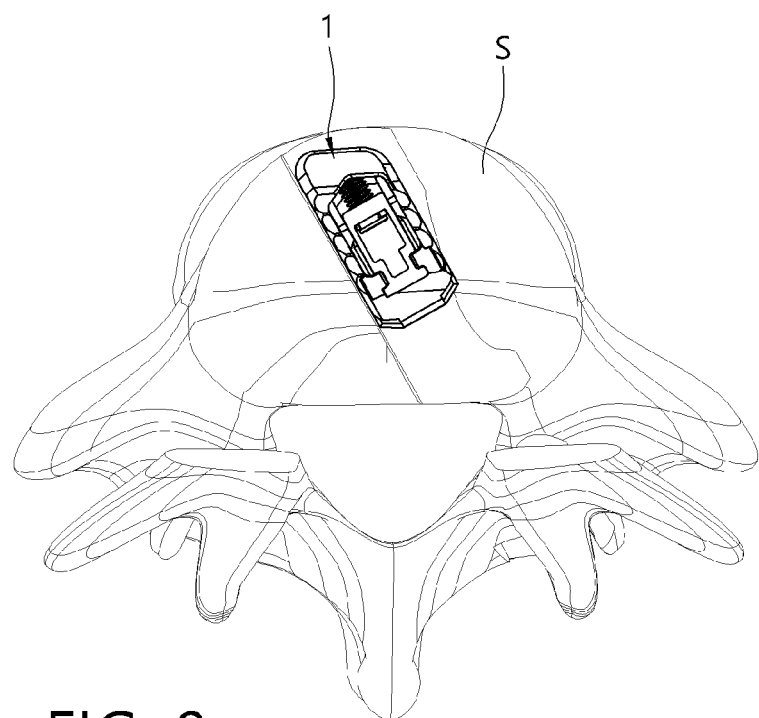
FIG. 9 is a view showing a state in which an intervertebral fusion cage according to an exemplary embodiment of the present invention is inserted into an intervertebral body.

FIG. 9 shows a state in which an intervertebral fusion cage 1 according to an exemplary embodiment of the present invention is inserted into an intervertebral body S. Referring to FIG. 9, the intervertebral fusion cage 1 is inserted from the rear to the front of a patient's intervertebral body S during surgery, and the front of the intervertebral body S is curved. In this case, the front inclined parts 143 and 153 respectively formed in front of the upper plate 14 and the lower plate 15 make the intervertebral fusion cage 1 to be in almost close contact along the curve of the front of the intervertebral body S. Through this, the intervertebral fusion cage 1 can be effectively arranged within the intervertebral body S. Specifically, the front inclined part 143 may be arranged parallel to a patient's coronal plane.

In addition, in an embodiment of the present invention, the upper plate 14 and the lower plate 15 include groove parts 144 and 154, respectively, formed to receive the screw thread part 132 of the screw 13 exposed forward through the screw hole 111 in a state in which the upper plate 14 and the lower plate 15 are coupled to the body 11, and the groove part 144 of the upper plate 14 and the groove part 154 of the lower plate 15 together form a through hole shape.

In addition, in an embodiment of the present invention, the upper plate 14 includes a keel part 145 formed parallel to the front inclined part 143 of the upper plate 14 at the upper portion, and the lower plate 15 includes a keel part 155 formed parallel to the front inclined part 153 of the lower plate 15 at the lower portion. Specifically, the keel parts 144 and 154 may be formed of protrusions and recesses that appear repeatedly over the front and rear in parallel with the front inclined parts 143 and 153.

When inserting the intervertebral fusion cage 1 into the intervertebral body, the keel part 145 of the upper plate 14 is embedded in an end plate located on the upper portion of the intervertebral body, and the keel part 155 of the lower plate 15 is embedded in an end plate located on the lower portion of the intervertebral body, thereby respectively providing a fixing force to the upper plate 14 and the lower plate 15.

As described above, according to an embodiment of the present invention, the front inclined parts 143 and 153 may be arranged parallel to a patient's coronal plane, and accordingly, the keel parts 145 and 155 formed parallel to the front inclined parts 143 and 153 may also be arranged parallel to the patient's coronal plane, and as a result, it is possible to secure physical stability by balancing the left and right when fixing the intervertebral fusion cage 1.

On the other hand, in an embodiment of the present invention, the upper plate 14 and the lower plate 15 include window parts 146 and 156 penetrated in the vertical direction, respectively. The window parts 146 and 156 are formed to penetrate vertically to provide a passage through which bone integration can be achieved between the intervertebral fusion cage 1 and the vertebral body. Bone integration between the implanted intervertebral fusion cage 1 and the vertebral body may be smoothly performed through the window parts 146 and 156.

Hereinafter, surgical instruments used for implantation of the intervertebral fusion cage 1 according to an embodiment of the present invention and an implantation process of the intervertebral fusion cage 1 using the same will be additionally described.

Figure 10:
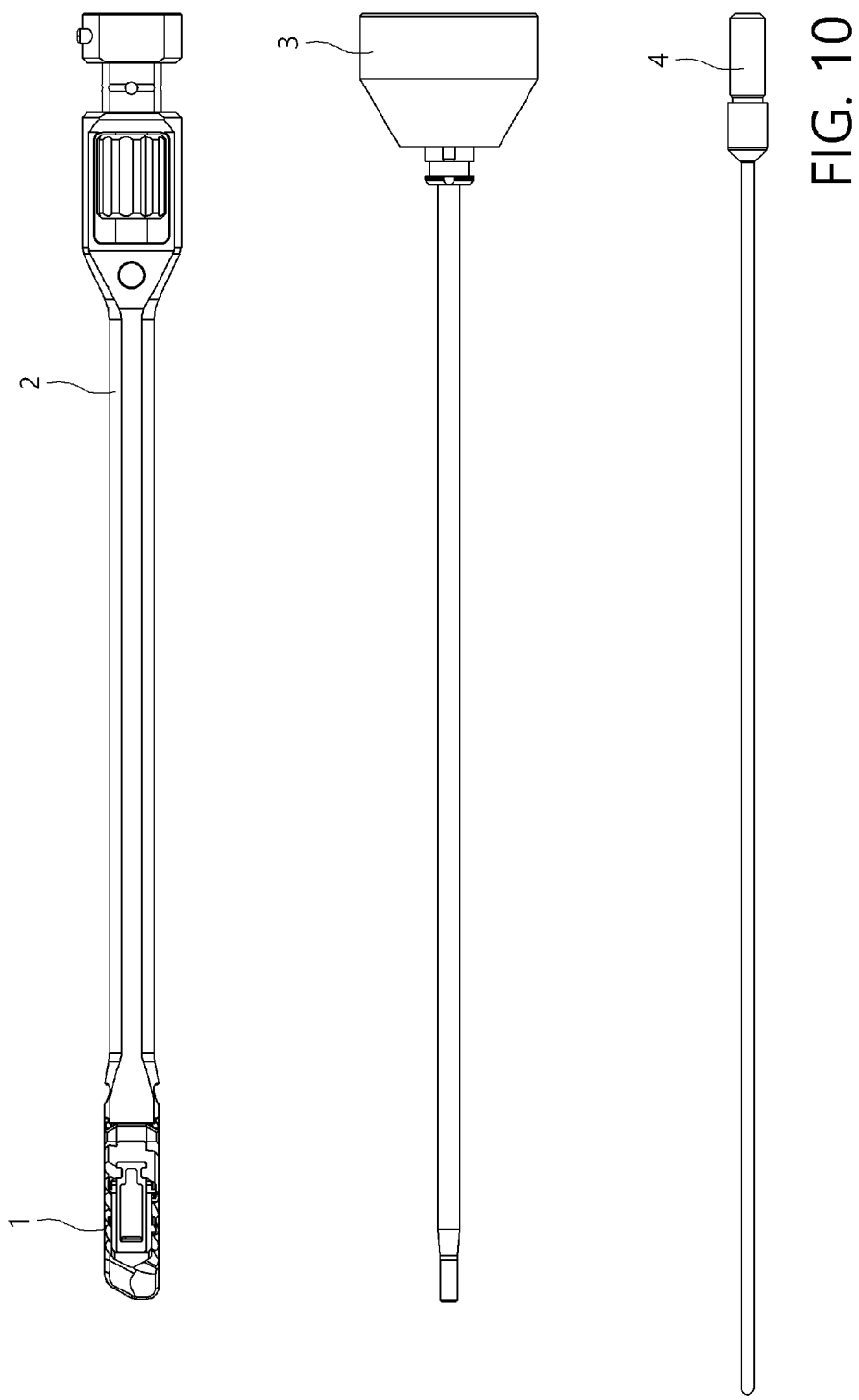
FIG. 10 is a view showing a coupling state of an intervertebral fusion cage according to an exemplary embodiment of the present invention and an inserter, a bone graft material cannula, and a bone graft material pusher.

FIG. 10 is a view showing a coupling state of an intervertebral fusion cage according to an exemplary embodiment of the present invention and an inserter, a bone graft material cannula, and a bone graft material pusher. In addition, FIG. 11 is a view showing a process of inserting an intervertebral fusion cage according to an exemplary embodiment of the present invention into a human body and injecting a bone graft material.

Referring to FIGS. 10 and 11, the inserter 2 is a surgical instrument for inserting the intervertebral fusion cage 1 into the human body, and has a hollow part formed through along the longitudinal direction. As described above, the front end of the inserter 2 may be coupled to the inserter coupling part 116 of the intervertebral fusion cage 1, and the intervertebral fusion cage 1 may be inserted into the intervertebral body S by the inserter 2.

In a state where the intervertebral fusion cage 1 is inserted into the intervertebral body S, the bone graft material cannula 3 may be inserted into the hollow part of the inserter 2 and the bone graft material B may be injected. Here, the bone graft material B may be allogenic bone, xenograft bone, demineralized bone, synthetic bone, or the like.

In this case, the bone graft material pusher 4 may be inserted into the bone graft material cannula 3 to push the bone graft material B toward the intervertebral fusion cage 1. Specifically, the bone graft material pusher 4 has a body part formed with an outer diameter equal to or less than the inner diameter of the bone graft material cannula 3, and be inserted into the bone graft material cannula 3 to push the bone graft material B inside the bone graft material cannula 3 toward the intervertebral fusion cage 1. The bone graft material (B) injected in this way fills the space inside the body 11 and the moving member 12, and can promote fusion of the intervertebral body.

Figure 12:
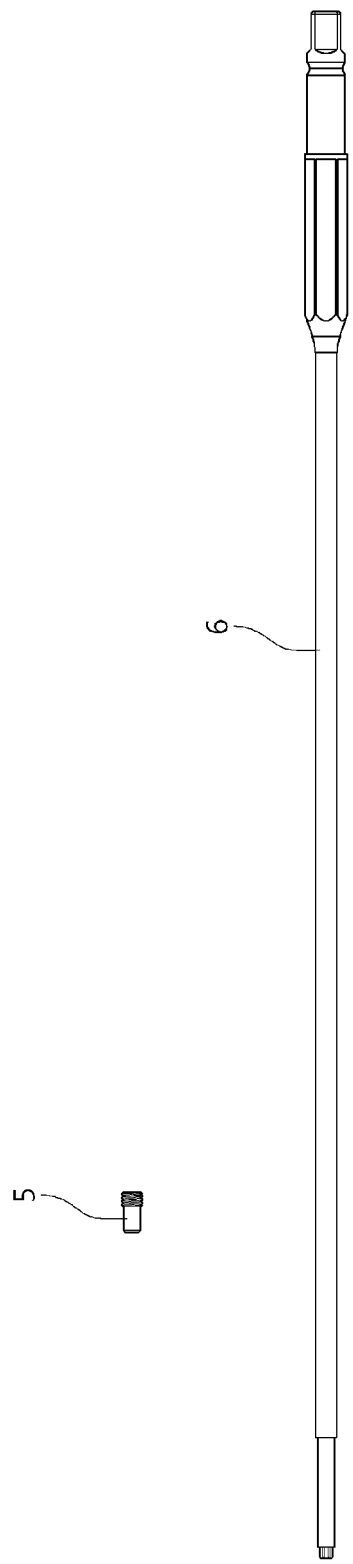
FIG. 12 is a view showing a locking screw and a locking screw driver used in a process of implanting an intervertebral fusion cage according to an exemplary embodiment of the present invention.

FIG. 12 is a view showing a locking screw and a locking screw driver used in a process of implanting an intervertebral fusion cage according to an exemplary embodiment of the present invention. In addition, FIG. 13 is a view showing a process of coupling a locking screw after inserting an intervertebral fusion cage according to an exemplary embodiment of the present invention into a human body and injecting a bone graft material.

Referring to FIG. 12 and FIG. 13, the locking screw 5 closes the rear of the intervertebral fusion cage 1 after the bone graft material B is injected into the intervertebral fusion cage 1. More specifically, the locking screw 5 has a shape capable of closing the rear hole 115 of the intervertebral fusion cage 1. The locking screw 5 may be coupled to the locking screw driver 6 to access the rear of the intervertebral fusion cage 1 through the hollow part of the inserter 2, and may be fastened to the rear, that is, the rear hole 115 of the intervertebral fusion cage 1 by the locking screw driver 6.

When the insertion of the intervertebral fusion cage 1 and the injection of the bone graft material B and the closing of the rear hole 115 by the locking screw 5 are completed, the inserter 2 is separated from the intervertebral fusion cage 1. The surgical site may then be sutured.

Although exemplary embodiments of the present invention have been described, the spirit of the present invention is not limited to the embodiments set forth herein. Those of ordinary skill in the art who understand the spirit of the present invention may easily propose other embodiments through supplement, change, removal, addition, etc. of elements within the same spirit, but the embodiments will be also within the scope of the present invention.

What is claimed is:
1. An intervertebral fusion cage, comprising:
 a body comprising a receiving part of which upper and lower portions have an opening, an upper guide part, and a lower guide part;
 a moving member disposed in the receiving part;
 a screw which is screw-coupled to the body and moves forwards or backwards relative to the body integrally with the moving member when rotating;
 an upper plate which has a guided part guided by the upper guide part and is disposed above the body while being engaged with the moving member; and a lower plate which has a guided part guided by the lower guide part and is disposed under the body while being engaged with the moving member, wherein the body further comprises a screw hole formed in a front of the body, and the screw comprises a head part rotatably coupled to the moving member and a screw thread part screwed to the screw hole, and wherein the moving member comprises a screw coupling hole formed so that the head part penetrates and is coupled to a front side of the moving member.

2. The intervertebral fusion cage of claim 1, wherein when the screw is rotated in one direction while the upper plate and the lower plate are fixed between the human body's vertebral bodies, as the body moves forward by the screw and the moving member, the upper plate moves upward along the upper guide part and the lower plate moves downward along the lower guide part.

3. The intervertebral fusion cage of claim 1, wherein the upper guide part is formed in a downwardly inclined form from a rear to a front in the upper portion of the body, and the lower guide part is formed in an upwardly inclined form from a rear to a front in the lower portion of the body.

4. The intervertebral fusion cage of claim 1, wherein the body further comprises a rear hole formed through a rear sidewall in communication with the receiving part, and the moving member further comprises a guide hole formed through the rear sidewall so that a screw rotation tool passing through the rear hole can enter the head part.

5. The intervertebral fusion cage of claim 4, wherein the rear hole provides a coupling interface of a surgical tool for insertion of the intervertebral fusion cage into the human body.

6. The intervertebral fusion cage of claim 1, wherein the moving member comprises grooves formed in a vertical direction on opposite sidewalls, respectively, and the upper plate and the lower plate each comprise a protrusion inserted into the groove, respectively.

7. The intervertebral fusion cage of claim 1, wherein the upper guide part and the lower guide part are formed on opposite sides of the body, respectively.

8. The intervertebral fusion cage of claim 1, wherein the upper plate and the lower plate each comprise front inclined parts formed to protrude forward from one side to the other side at a front.

9. The intervertebral fusion cage of claim 8, wherein the upper plate and the lower plate are formed vertically symmetrical.

10. The intervertebral fusion cage of claim 9, wherein the upper plate and the lower plate comprise a keel part formed parallel to the front inclined part at the upper portion and the lower portion, respectively.

11. The intervertebral fusion cage of claim 1, wherein the upper plate and the lower plate comprise window parts, respectively, penetrated in the vertical direction.

12. The intervertebral fusion cage of claim 11, wherein the body is formed to be surrounded on all sides by sidewalls and open up and down.

* * * * *